United States Patent
Bhattacharya et al.

(10) Patent No.: US 6,566,504 B2
(45) Date of Patent: *May 20, 2003

(54) PROCESS FOR VIRAL INACTIVATION OF LYOPHILIZED BLOOD PROTEINS

(75) Inventors: Prabir Bhattacharya, Walnut, CA (US); Toshiharu Motokubota, Arcadia, CA (US); Norman M. Fedalizo, Rowland Heights, CA (US)

(73) Assignee: Alpha Therapeutic Corporation, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/894,346

(22) Filed: Jun. 28, 2001

(65) Prior Publication Data

US 2001/0047085 A1 Nov. 29, 2001

Related U.S. Application Data

(62) Division of application No. 09/166,875, filed on Oct. 6, 1998, which is a continuation of application No. 08/634,921, filed on Apr. 19, 1996, now abandoned.

(51) Int. Cl.[7] ............................................. C07K 14/755
(52) U.S. Cl. ....................................................... 530/383
(58) Field of Search ........................................ 530/383

(56) References Cited

U.S. PATENT DOCUMENTS

| | | | |
|---|---|---|---|
| 3,459,731 | A | 8/1969 | Gramera et al. |
| 4,089,944 | A | 5/1978 | Thomas |
| 4,178,454 | A | 12/1979 | Naruto et al. |
| 4,188,318 | A | 2/1980 | Shanbrom |
| 4,297,344 | A | 10/1981 | Schwinn et al. |
| 4,359,463 | A | 11/1982 | Rock |
| 4,369,184 | A | 1/1983 | Stokbroekx et al. |
| 4,371,673 | A | 2/1983 | Pitha |
| 4,511,651 | A | 4/1985 | Beaty et al. |
| 4,596,795 | A | 6/1986 | Pitha |
| 4,650,678 | A | 3/1987 | Fuhge et al. |
| 4,659,696 | A | 4/1987 | Hirai et al. |
| 4,727,064 | A | 2/1988 | Pitha |
| 4,751,095 | A | 6/1988 | Karl et al. |
| 4,764,604 | A | 8/1988 | Müller |
| 4,870,060 | A | 9/1989 | Müller |
| 4,876,244 | A | 10/1989 | Umezawa et al. |
| 4,877,778 | A | 10/1989 | Carpenter et al. |
| 4,925,678 | A | 5/1990 | Ranney |
| 4,956,274 | A | 9/1990 | Khanna et al. |
| 4,956,351 | A | 9/1990 | Mesens et al. |
| 4,971,797 | A | 11/1990 | Cherukuri et al. |
| 4,985,242 | A | 1/1991 | Sekine et al. |
| 5,024,998 | A | 6/1991 | Bodor |
| 5,068,227 | A | 11/1991 | Weinshenker |
| 5,070,081 | A | 12/1991 | Majid et al. |
| 5,087,461 | A | 2/1992 | Levine et al. |
| 5,096,893 | A | 3/1992 | Pitha et al. |
| 5,120,720 | A | 6/1992 | Pitha et al. |
| 5,134,127 | A | 7/1992 | Stella et al. |
| 5,147,756 | A | 9/1992 | Fodor |
| 5,173,481 | A | 12/1992 | Pitha et al. |
| 5,183,809 | A | 2/1993 | Weisz et al. |
| 5,192,743 | A | 3/1993 | Hsu et al. |
| 5,221,669 | A | 6/1993 | Anand et al. |
| 5,221,695 | A | 6/1993 | Finch et al. |
| 5,229,146 | A | 7/1993 | Tanaka |
| 5,281,579 | A | 1/1994 | Estep |
| 5,290,831 | A | 3/1994 | Di Ruocco et al. |
| 5,298,410 | A | 3/1994 | Phillips et al. |
| 5,300,280 | A | 4/1994 | DeRosch et al. |
| 5,324,718 | A | 6/1994 | Loftsson |
| 5,334,382 | A | 8/1994 | Phillips et al. |
| 5,348,941 | A | 9/1994 | Middaugh et al. |
| 5,354,560 | A | 10/1994 | Lovrecich |
| 5,376,632 | A | 12/1994 | Konings et al. |
| 5,376,645 | A | 12/1994 | Stella et al. |
| 5,399,670 | A | 3/1995 | Bhattacharya et al. |
| 5,426,184 | A | 6/1995 | Pitha et al. |
| H1509 | H | 12/1995 | Eran et al. |
| 5,659,017 | A * | 8/1997 | Bhattacharya et al. ...... 530/383 |

FOREIGN PATENT DOCUMENTS

| | | |
|---|---|---|
| CA | 1222697 | 6/1987 |
| EP | 0149197 | 7/1985 |
| GB | 856792 | 12/1960 |
| JP | 57004914 | 1/1982 |
| JP | 59104556 | 6/1984 |
| JP | 4264020 | 9/1992 |
| JP | 7069887 | 3/1995 |
| WO | WO 8203871 | 11/1982 |
| WO | 82/03871 | * 11/1982 |
| WO | WO 8502767 | 7/1985 |
| WO | WO 9003784 | 4/1990 |
| WO | WO 9214762 | 9/1992 |
| WO | WO 9319061 | 9/1993 |
| WO | WO 9508993 | 4/1995 |

OTHER PUBLICATIONS

Fukunaka, K. et al., "Aluminum –Cyclodextrin Sulphate as a Stabilizer and Sustained–release Carrier for Basic Fibroblast Growth Factor," J. Pharm. Pharmacol. 1994, 46: 168–171.

Brewster, M.E. et al., "Use of 2–Hydroxypropyl—cyclodextrin as a Solubilizing and Stabilizing Excipient for Protein Drugs," Pharmaceutical Research, vol. 8, No. 6, 1991.

(List continued on next page.)

Primary Examiner—Michael Borin
(74) Attorney, Agent, or Firm—Christie, Parker & Hale, LLP

(57) ABSTRACT

A process for inactivating viral contaminants of lyophilized Factor VIII by heat is provided. The process comprises forming a stable complex between the Factor VIII and a cyclodextrin in an aqueous solution. The solution is then lyophilized, and the Factor VIII/cyclodextrin complex is recovered. The lyophilized Factor VIII/cyclodextrin is then heated to 60° C. to inactivate any virus present. The material may then be reconstituted prior to administration to a patient.

18 Claims, 3 Drawing Sheets

OTHER PUBLICATIONS

"Cavitron Cyclo–dextrins" (advertisement), Amaizo American Maize–Products Company, CE & N, Jan.–Apr. 1992.

Ressing, M.E. et al., "The Influence of Sucrose, Dextran, and Hydroxypropyl–β–cyclodextrin as Lyoprotectants for a Freeze–Dried Mouse $IgG_{2a}$ Monoclonal Antibody (MN12)", Pharmaceutical Research, vol. 9, No. 2, 1992.

Hora, M.S., "Development of a Lyophilized Formulation of Interleukin–2," International Symposium on Biological Product Freeze–Drying and Formulation, Bethesda, USA, 1990, Develop. biol. Standard., vol. 74, pp. 295–306 (Karger, Basel, 1991).

Charman, S.A. et al., "Techniques for Assessing the Effects of Pharmaceutical Excipients on the Aggregation of Porcine Growth Hormone," Pharmaceutical Research, vol. 10, No. 7, 1993.

Hora, M.S. et al., "Lyophilized Formulations of Recombinant Tumor Necrosis Factor," Pharmaceutical Research, vol. 9, No. 1, 1992.

"Encapsin HPB, R81 216 hydroxypropyl–β–cyclodextrin, A Real Solution for Real Drug Delivery Problems," Jannsen Biotech, N.V., Olen, Belgium.

* cited by examiner

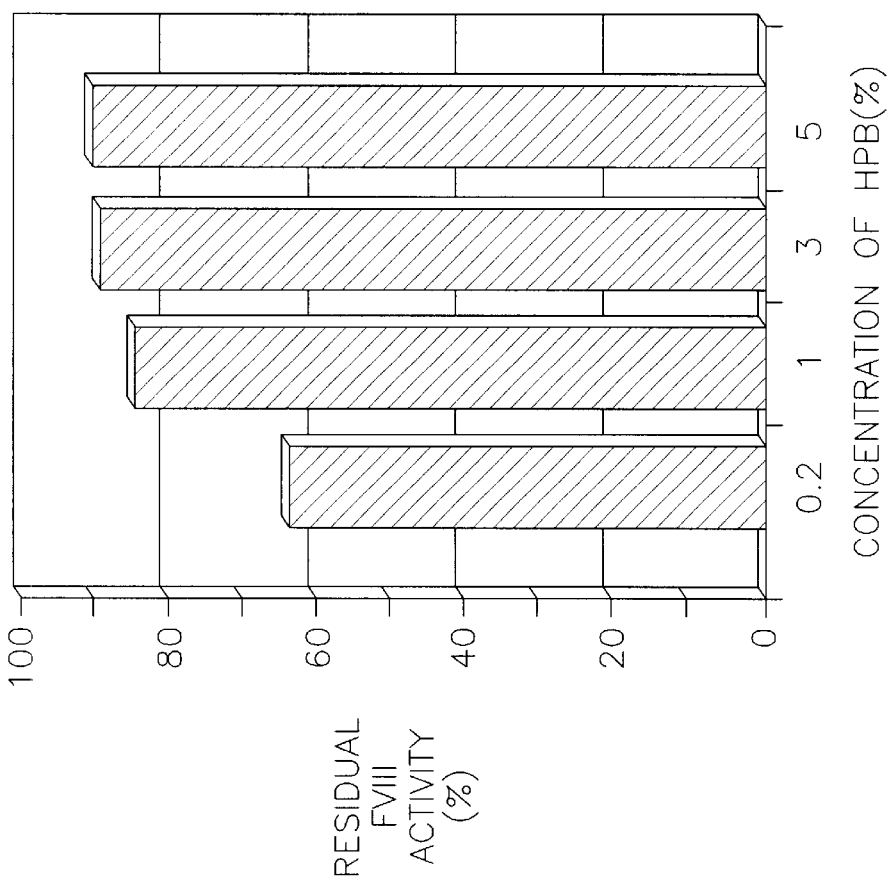

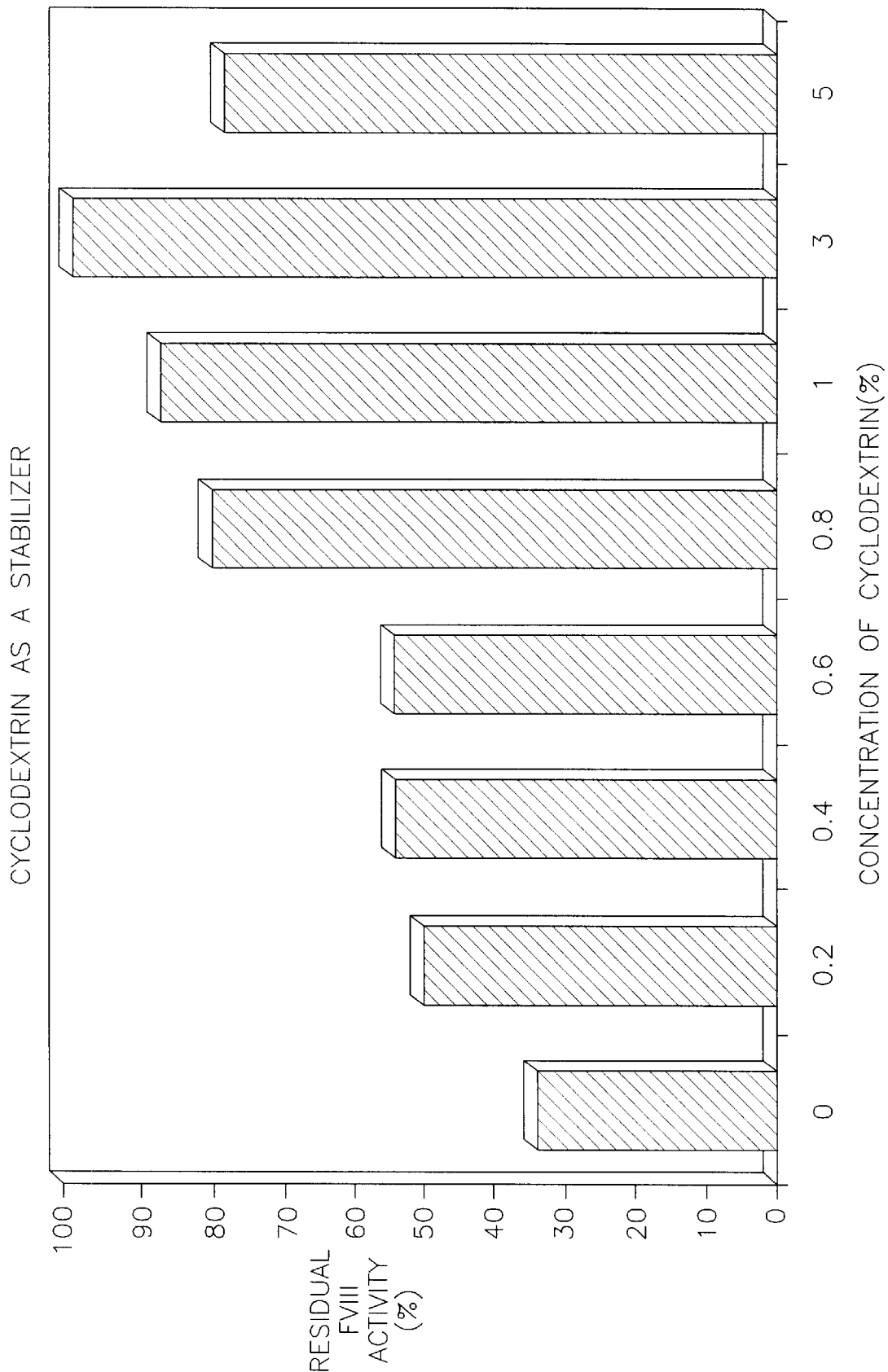

PROCESS FOR VIRAL INACTIVATION OF LYOPHILIZED BLOOD PROTEINS

CROSS-REFERENCE TO RELATED APPLICATIONS

The present application is a division of co-pending application Ser. No. 09/166,875, filed Oct. 6, 1998, which is a continuation of application Ser. No. 08/634,921, filed Apr. 19, 1996, now abandoned.

FIELD OF THE INVENTION

The present invention relates to inactivating viral contaminants of pharmaceutical preparations. More specifically, the present invention is directed to a process for inactivation of viral contaminants of lyophilized blood proteins, particularly Factor VIII, by heat.

BACKGROUND OF THE INVENTION

The primary therapeutic use of Factor VIII has been its intravenous administration to hemophilia A patients. In severe cases, relatively high concentrations of Factor VIII are required. These high concentrations are obtained by purification and concentration of Factor VIII. Factor VIII is commercially available as a lyophilized sterile dry powder which is reconstituted with sterile distilled water or sterile physiological saline for infusion into a hemophilia A patient.

Any viral contaminants in Factor VIII must be inactivated before the Factor VIII preparation can be clinically used so that the spread of HIV, hepatitis, etc., is prevented. There are a number of different approaches to inactivating viruses in Factor VIII. One approach is to heat the lyophilized product to at least 60° C. for at least 10 hours. Commonly, the lyophilized products are heated at 60° C. or even 80° C. for 72 hours. It has been found that a lyophilized, heat-treated Factor VIII product takes longer than desired to be reconstituted, and, additionally, the Factor VIII product can lose a substantial portion of its activity during the lyophilization and heating process. Accordingly, heating lyophilized Factor VIII for extended periods, e.g., 80° C. for 72 hours, to effect viral inactivation is not a preferred approach.

SUMMARY OF THE INVENTION

The present invention provides a process for stabilizing lyophilized blood proteins, particularly lyophilized Factor VIII, during viral inactivation by heat. The process comprises providing an aqueous solution of a blood protein. Cyclodextrin is added to the solution in an amount sufficient to form a complex with at least a portion of, and preferably all of the blood protein. The solution is then lyophilized to provide a dry blood protein/cyclodextrin complex.

The lyophilized blood protein/cyclodextrin complex is then heated to a temperature and for a time sufficient to inactivate any viral contaminants, preferably to a temperature of at least about 60° C. and more preferably to at least about 80° C. for a time of at least about 10 hours and preferably at least about 72 hours. The viral inactivated blood protein/cyclodextrin complex may be thereafter reconstituted to provide a solution of the blood protein administratable to a patient.

It has been discovered that the stabilization of blood protein with cyclodextrin prior to lyophilization results in a dramatic reduction of denaturation of the protein during dry heat viral inactivation. Additionally, the reconstitution time for the lyophilized blood protein stabilized in accordance with practice of the present invention is substantially reduced, with an attendant reduction of insoluble precipitates.

BRIEF DESCRIPTION OF THE DRAWINGS

These and other features, aspects and advantages of the present invention will become better understood with reference to the following description, appended claims, and accompanying drawings wherein:

FIG. 2 is a bar chart setting forth residual Factor VIII activity as a function of the concentration of hydroxy propyl β-cyclodextrin; and FIG. 3 is a bar chart setting forth the residual Factor VIII activity as a function of the concentration of cyclodextrin.

DETAILED DESCRIPTION

The present invention is directed to a process which incorporates the use of various cyclodextrins to stabilize lyophilized proteins during dry heat viral inactivation and to help reconstitute these proteins after viral inactivation. Blood proteins with which the present process may be used include, but are not limited to, albumin, Factor II, Factor VII, Factor VIII, Factor IX, Factor X and $X_a$, fibrinogen, antithrombin III, transferrin, haptoglobin, gamma globulins, fibronectin, protein C, protein S and thrombin.

Cyclodextrins are a group of homologous oligosaccharides that are obtained from starch by the action of enzymes from *Bacillus macerans*. They are cyclic molecules containing six or more α-D-glucopyranose units linked together at the 1, 4 positions as in amylose. This cyclic structure may also be referred to as a torus.

The cyclodextrins useful in the practice of this invention are the α-, β- and γ-cyclodextrins which are composed, respectively, of six, seven and eight α-D-glucopyranose units as well as derivatives, such as hydroxypropyl-β-cyclodextrin.

Figure 1C:
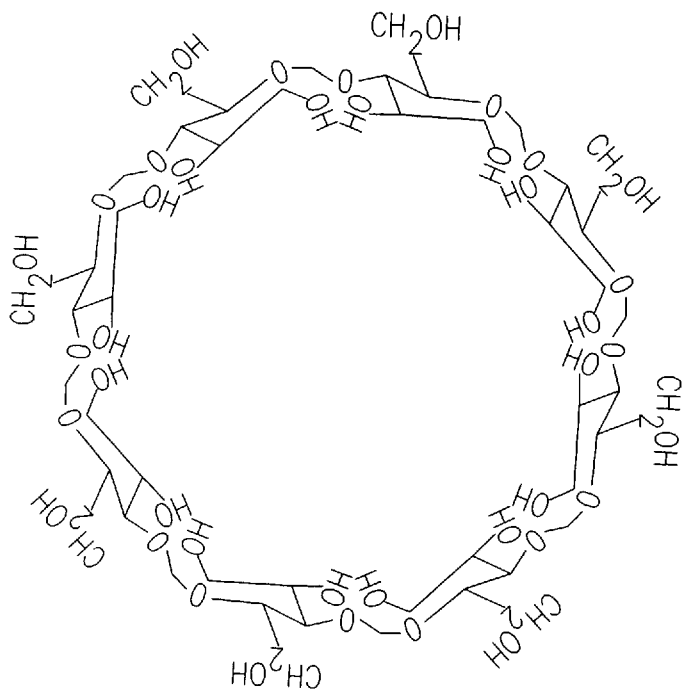
FIGS. 1A–1C illustrate α-cyclodextrin, β-cyclodextrin, and γ-cyclodextrin, respectively.
Figure 1B:
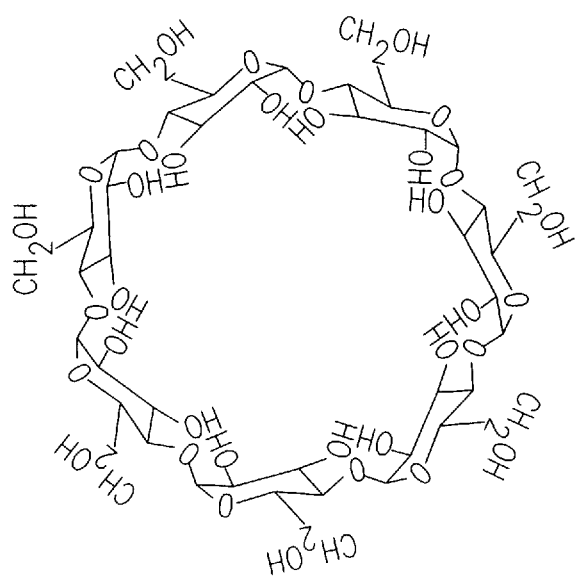
Figure 1A:
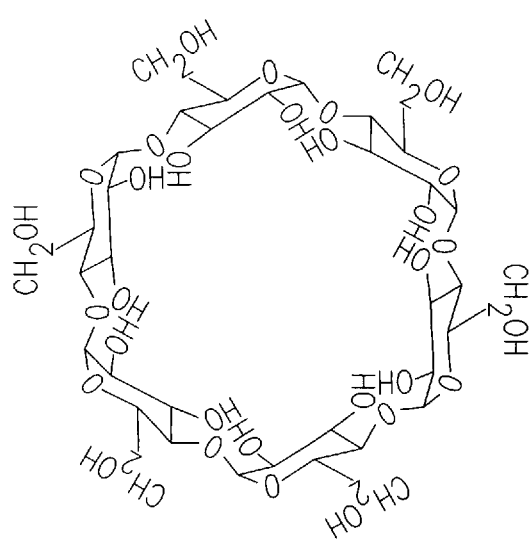

FIGS. 1a, 1b, and 1c illustrate the structure of the three most common cyclodextrins. α-Cyclodextrin has six glucopyranose units, β-cyclodextrin has seven glucopyranose units, and γ-cyclodextrin has eight glucopyranose units. Mixtures of these materials are included in the term "cyclodextrin" as used herein.

The cyclodextrin may be added to an aqueous solution containing the blood protein before lyophilization at any suitable point in the purification process. Preferably, the cyclodextrin is added to an aqueous solution of the blood protein after all purification steps have been completed. This is done to prevent the cyclodextrin from forming a complex with impurities thereby making removal of the impurities more difficult.

The cyclodextrin is added in an amount sufficient to assure the formation of a complex with all of the desired blood protein. An amount of cyclodextrin which provides an aqueous solution having a cyclodextrin concentration of at least about 0.1%, preferably from about 0.8% to about 5% weight to volume (wt/vol.) and more preferably about 3% wt/vol. is suitable for most applications.

It has been found that the presence of cyclodextrin during dry heat viral inactivation of the lyophilized blood protein substantially reduces denaturation of the blood protein. The residual activity of the blood protein after dry heat viral inactivity at 80° C. for 72 hours and reconstitution is at least 90% and preferably at least 95% and even more preferably at least about 98% of the activity of the blood protein before viral inactivation.

It has also been found that the reconstitution time is substantially reduced by the presence of cyclodextrin during lyophilization and dry heat inactivation.

EXAMPLE 1

General Procedure for Preparation of Factor VIII

In an exemplary embodiment, the starting material for the Factor VIII lyophilizate is plasma, frozen to a temperature of about −20° C. The plasma was thawed to 0° to 5° C., during which time a precipitate formed (the cryoprecipitate) which was removed by centrifugation and recovered for further purification and concentration.

The cryoprecipitate was suspended in heparinized distilled water (250 units of heparin or less per mL) and mixed at 25±10° C. until well suspended and the pH of the solution was adjusted to 7.0±1.0 with dilute HCl. The volume of heparinized distilled water used was 6±4 liters per kilogram of cryoprecipitate.

PEG was then added to the solution to a final concentration of 3±2% and was mixed at 25±10° C. The pH of the suspension was then adjusted to 6.5±1.0 with dilute acetic acid. The suspension was mixed at 25±10° C. for not less than 15 minutes. The precipitate formed was removed by centrifugation.

The recovered supernatant from centrifugation was filtered to remove any solid particles to thereby form a filtered Factor VIII solution. Tri(n-butyl) phosphate (TNBP) and Polysorbate 80 were added to the filtered Factor VIII solution to a final concentration of 0.30±0.02% TNBP v/w and 1.00±0.05% polysorbate 80 w/w. The pH of the mixture was adjusted to 6.5±1.0 with dilute acetic acid or sodium hydroxide. The product was then transferred to a viral control area following 1 hour incubation at 27° C.±3° C. The suspension was mixed at 27° C.±3° C. for not less than six hours and not more than 12 hours to form a solvent detergent (SD) Factor VIII solution.

The SD Factor VIII solution was loaded into a QAE-55OC anion exchange chromatography column with a binding buffer comprising 0.35 M NaCl and 0.025 M histidine at a pH of 6.8. The column was washed with a washing buffer comprising 0.35 M NaCl and 0.025 M histidine at a pH of 6.8 and then washed again with a washing buffer comprising 0.1 M $CaCl_2$ and 0.025 M histidine at a pH of 6.8. Factor VIII was eluted with an elution buffer comprising 0.2 M $CaCl_2$ and 0.025 M histidine at a pH of 6.8. The Factor VIII was then further purified using glycine and NaCl to precipitate out Factor VIII. Glycine was added to the eluate to a final concentration of 2 M and then NaCl was added to a final concentration of 1.6 M. The mixture was then incubated for 2 hours at room temperature. The mixture was then centrifuged and the Factor VIII precipitate recovered. The Factor VIII complex precipitate was reconstituted in a solution of 0.1 M arginine and 0.025 M histidine at a pH of 7.3. This solution is also referred to as "purified bulk." The Factor VIII activity in the bulk solution was measured and this solution was then used for further processing.

EXAMPLE 2

In this example, a sterile Factor VIII bulk solution of Example 1 with the specific activity of 370 units per milligram was filled into vials with various additives and then lyophilized. The lyophilized Factor VIII product was then subjected to dry-heating (DH) (80° C. for 72 hours). The final preparations were reconstituted with water for injection. Reconstitution time and residual Factor VIII activity were measured by a one stage clotting assay. The results of the tests, which are set forth in Table I below, show that Factor VIII which was lyophilized from the solution comprising 3% cyclodextrin (hydroxypropyl-β-cyclodextrin) was more stable than the Factor VIII prepared using various amounts of other materials, such as albumin, Tween 80, PEG, glycine, sodium citrate, dextrin, and histidine.

TABLE I

Screening of Additive for Highly Purified Factor VIII

| Additive | F.VIII: U/ml before DH | F.VIII: U/ml after DH | Recon. time (sec) after DH |
|---|---|---|---|
| No additive | 77.5 (100%) | 45.1 (58%) | 20 |
| 0.1% Tween 80 | 71.8 (") | 18.4 (26%) | 12 |
| 0.1% PEG | 83.2 (") | 13.8 (17%) | >10 min |
| 0.2M glycine | 78.8 (") | 42.1 (53%) | 15 |
| 0.2M Na citrate | 92.8 (") | 26.1 (28%) | 60 |
| 3% cyclodextrin | 75.8 (") | 74.5 (98%) | <10 |
| 3% dextrin | 79.2 (") | 43.1 (54%) | 22 |
| 0.1M histidine | 70.9 (") | 51.0 (72%) | 10 |

EXAMPLE 3

In a similar experiment, control and test solutions using 0.5% albumin and 3% cyclodextrin as additives were prepared. The solutions were lyophilized, and lyophilized samples were then subjected to dry-heating at 80° C. for 72 hours. The results of the test are shown in Table II below. It appears that Factor VIII associated with 3% cyclodextrin was substantially more stable when dry-heated than with the Factor VIII stabilized with 0.5% albumin alone.

TABLE II

Activity of the Product in Dry-Heating Step

| Additive | Dry heating (80° C., 72 hr) | F.VIII:C. U/ml (%) |
|---|---|---|
| No additive | before DH | 132 (100) |
| | after DH | 86 (65) |
| 0.5%-albumin | before DH | 128 (100) |
| | after DH | 98 (77) |
| 3%-cyclodextrin (HPB) | before DH | 127 (100) |
| | after DH | 114 (90) |

EXAMPLE 4

In another test, the optimum concentration of hydroxypropyl-β-cyclodextrin used to stabilize Factor VIII was studied by measuring residual Factor VIII activity as a function of the concentration of cyclodextrin used in the solution prior to lyophilization and dry-heating. The results, which are set forth in FIG. 2, show that at a 0.2% cyclodextrin concentration, Factor VIII residual activity was approximately 62%; at 3% cyclodextrin concentration, Factor VIII activity was about 90%, while at a 5% cyclodextrin concentration, residual activity was approximately 91%.

EXAMPLE 5

In another test Factor VIII was stabilized with three different cyclodextrins, namely, hydroxypropyl-β-cyclodextrin at 3%, methylether-β-cyclodextrin at 3%, and γ-cyclodextrin at 3%. Results of this test, which are set forth below in Table III, show that each of the three different cyclodextrin used were effective in stabilizing Factor VIII.

TABLE III

| Additive | Dry heating (80° C., 72 hr) | F.VIII:C. U/ml (%) |
|---|---|---|
| 3% hydroxypropyl-β-cyclodextrin (HPB) | before DH | 58 (100) |
| | after DH | 52 (90) |
| 3% methyl ethers-β-cyclodextrin | before DH | 68 (100) |
| | after DH | 69 (101) |
| 3% γ-cyclodextrin | before DH | 54 (100) |
| | after DH | 61 (113) |

EXAMPLE 6

In yet another test, the optimum concentration of hydroxypropyl-β-cyclodextrin used to stabilize Factor VIII was studied by measuring residual Factor VIII activity in lyophilized Factor VIII after dry heating at 80° C. for 72 hours as a function of the concentration of cyclodextrin used in the solution from which the lyophilized product was prepared. The results, which are set forth in FIG. 3, show that at 0.2% cyclodextrin concentration, Factor VIII residual activity was approximately 50%; at 3% cyclodextrin concentration, Factor VIII residual activity was approximately 97% to 98%; while at 5% cyclodextrin concentration, Factor VIII residual activity dropped to approximately 76% to 77%.

The above descriptions of exemplary embodiments of processes for preparing stabilized Factor VIII products are for illustrative purposes. Because of variations which will be apparent to those skilled in the art, the present invention is not intended to be limited to the particular embodiments described above. This invention can also be practiced in the absence of any element not specifically disclosed. The scope of the invention is described in the following claims.

What is claimed is:

1. A process for inactivating viral contaminants of Factor VIII comprising the steps of:
   (a) providing an aqueous solution of Factor VIII;
   (b) adding to the solution a cyclodextrin in an amount sufficient to form a stable complex with the Factor VIII;
   (c) lyophilizing the solution of step (b) and recovering lyophilized Factor VIII/cyclodextrin complex; and
   (d) heating the lyophilized Factor VIII/cyclodextrin complex to at least 60° C. for a time sufficient to inactivate any viruses present in the Factor VIII/cyclodextrin complex.

2. The process according to claim 1 wherein the cyclodextrin is selected from the group consisting of α-cyclodextrin, β-cyclodextrin, and γ-cyclodextrin, and mixtures thereof.

3. The process according to claim 1 wherein the cyclodextrin is added in an amount sufficient to provide a cyclodextrin concentration of at least about 0.1% (wt/vol).

4. The process according to claim 1 wherein the lyophilized Factor VIII/cyclodextrin complex recovered from step (c) is heated to a temperature of at least about 60° C. for at least about 10 hours.

5. The process according to claim 1 wherein the lyophilized Factor VIII/cyclodextrin complex recovered from step (c) is heated to a temperature of at least about 80° C. for at least about 72 hours.

6. The process according to claim 1 further comprising the step of reconstituting the lyophilized Factor VIII/cyclodextrin complex.

7. The process according to claim 1 wherein cyclodextrin is added to the solution of step (a) to a concentration of from about 0.8% to about 5% (wt./vol.).

8. The process according to claim 1 wherein the cyclodextrin is added to the solution of step (a) to a concentration of about 3% (wt./vol.).

9. The process according to claim 6 wherein the residual activity of the Factor VIII after lyophilization, heating and reconstitution is at least about 90% of the activity of the Factor VIII before lyophilization.

10. The process according to claim 6 wherein the residual activity of the Factor VIII after lyophilization, heating and reconstitution is at least about 95% of the activity of the Factor VIII before lyophilization.

11. A process for inactivating viral contaminants of Factor VIII comprising the steps of:
   (a) providing an aqueous solution of Factor VIII;
   (b) adding to the solution a cyclodextrin selected from the group consisting of α-cyclodextrin, β-cyclodextrin, or γ-cyclodextrin, so that the solution has a cyclodextrin concentration of from about 0.1% to about 3% (wt/vol) to thereby form a Factor VIII/cyclodextrin complex;
   (c) lyophilizing the solution of step (b) and recovering lyophilized Factor VIII/cyclodextrin complex; and
   (d) heating the lyophilized Factor VIII/cyclodextrin complex to at least 60° C. for a time sufficient to inactivate any viruses present in the Factor VIII/cyclodextrin complex.

12. The process according to claim 11 wherein the lyophilized Factor VIII/cyclodextrin complex recovered from step (c) is heated to a temperature of at least about 60° C. for at least about 10 hours.

13. The process according to claim 11 wherein the lyophilized Factor VIII/cyclodextrin complex recovered from step (c) is heated to a temperature of at least about 80° C. for at least about 72 hours.

14. The process according to claim 11 further comprising the step of reconstituting the lyophilized Factor VIII/cyclodextrin complex.

15. The process according to claim 11 wherein cyclodextrin is added to the solution of step (a) to a concentration of from about 0.8% to about 5% (wt./vol.).

16. The process according to claim 11 wherein the cyclodextrin is added to the solution of step (a) to a concentration of about 3% (wt./vol.).

17. The process according to claim 14 wherein the residual activity of the Factor VIII after lyophilization, heating and reconstitution is at least about 90% of the activity of the Factor VIII before lyophilization.

18. The process according to claim 14 wherein the residual activity of the Factor VIII after lyophilization, heating and reconstitution is at least about 95% of the activity of the Factor VIII before lyophilization.

* * * * *